(12) United States Patent
Aunio et al.

(10) Patent No.: US 8,790,383 B2
(45) Date of Patent: *Jul. 29, 2014

(54) LIGHT THERAPY MODALITY

(71) Applicant: Valkee Oy, Oulunsalo (FI)

(72) Inventors: Antti Aunio, Oulu (FI); Juuso Nissila, Ii (FI)

(73) Assignee: Valkee Oy, Oulunsalo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 13/896,673

(22) Filed: May 17, 2013

(65) Prior Publication Data

US 2013/0253618 A1  Sep. 26, 2013

Related U.S. Application Data

(63) Continuation of application No. 13/074,230, filed on Mar. 29, 2011, now Pat. No. 8,465,531.

(51) Int. Cl.
*A61N 5/06* (2006.01)

(52) U.S. Cl.
CPC ....... *A61N 5/0618* (2013.01); *A61N 2005/0605* (2013.01); *A61N 2005/0647* (2013.01); *A61N 5/0622* (2013.01); *A61N 2005/0662* (2013.01)
USPC .................... 607/89; 607/88; 607/91; 607/93

(58) Field of Classification Search
CPC .......................... A61N 5/062; A61N 2005/067
USPC ........................................ 607/88–93; 351/51
See application file for complete search history.

(56) References Cited

U.S. PATENT DOCUMENTS

| | | |
|---|---|---|
| 5,167,228 A | 12/1992 | Czeisler et al. |
| 6,350,275 B1 | 2/2002 | Vreman et al. |
| 7,534,255 B1 | 5/2009 | Streeter et al. |
| 2005/0137656 A1 | 6/2005 | Malak |
| 2006/0064144 A1 | 3/2006 | Chen et al. |
| 2007/0167999 A1 | 7/2007 | Breden et al. |
| 2010/0179469 A1 | 7/2010 | Hammond et al. |
| 2011/0313499 A1 | 12/2011 | Smith et al. |

FOREIGN PATENT DOCUMENTS

| | | |
|---|---|---|
| EP | 1074275 | 7/2001 |
| JP | 2009034349 | 2/2009 |
| WO | 9851372 | 11/1998 |
| WO | 2006134339 | 12/2006 |
| WO | 2008029001 | 3/2008 |
| WO | 2009020862 | 2/2009 |

OTHER PUBLICATIONS

Vaaraniemi, A. "Test: Valkee Bright Light Headset Causes a Burning Feeling" Digitoday, Nov. 24, 2010, pp. 1-4.
Vaaraniemi, A. "Test: Valkee Bright Light Headset Causes a Burning Feeling" Digitoday—English Translation.

*Primary Examiner* — William Thomson
*Assistant Examiner* — Jeffrey Lipitz
(74) *Attorney, Agent, or Firm* — Tarolli, Sundheim, Covell & Tummino LLP

(57) ABSTRACT

A method of light therapy includes non-invasive, intra-cranial administration of bright light via the ear canal of a subject by using a light intensity of 0.7-12 lumens, and a treatment time of 1-15 minutes. A medical device including radiation elements for directing the light via the ear canal for use in the light therapy is described.

10 Claims, 1 Drawing Sheet

\* p-value<0.05 compared with week 0

LIGHT THERAPY MODALITY

RELATED APPLICATION

The present invention is a continuation of U.S. patent application Ser. No. 13/074,230, filed 29 Mar. 2011 and titled "Light Therapy Modality", the entire contents of which are incorporated herein by reference.

FIELD OF THE INVENTION

The present invention relates to light therapy, and especially to light therapy intra-cranially via the ear canal. A medical device for use in the therapy is described.

BACKGROUND OF THE INVENTION

Conventional light therapy comprises exposing a person, and especially the face to bright light, whereby the light is believed to be transported into the brain via the ocular route i.e. through the eyes. The drawback of conventional light therapy is that the amount of light required may be so high that delivering it via the ocular route may cause damage to the eye nerve, headache and other harmful side effects. Another drawback is that the recommended treatment time is at least half an hour, and preferably at least one hour, which limits a person's daily life. The person should also be very close to the light device to realize a therapeutic effect, preferably as close as 10-20 inches (30-50 cm), which makes administration cumbersome. Traditional light therapy lamps also must produce 2,500-10,000 lux, making these light units very high in energy consumption. Late19-11y alternative routes for light therapy have been proposed. However, the knowledge of their effect is very limited and clinical evidence on treatment modalities like dosing or clinical intensities that would be needed for effective treatment have not been studied.

WO98/51372 discloses a method of resetting the circadian clock by applying non-solar photic stimulation of 15 to 150,000 lux, preferably 10,000 to 13,000 lux to any non-ocular region of the human body for 15 minutes to about 12 hours, preferably for 3 hours. Such treatment is hard to carry out without affecting normal activity. A method and device for directing optical radiation energy non-invasively at intra-cranial nerve tissue of a user through an external auditory canal is disclosed in WO2008/029001. The device is suggested for use e.g. in changing diurnal rhythm, in treating jetlag, sleep irregularity, seasonal affective disorder (SAD) etc. No details of treatment modalities are given. Another device for irradiating the inside of the auditory meatus with light is disclosed in JP2009034349.

The mode of action of light therapy is to an extent unknown. This is at least partly due to the fact that there is no easy way to measure the treatment effects induced or the very accurate amount of light delivered to treat a condition or to induce a desired treatment effect. A problem with light therapy is therefore that little is known about the dose of light needed to achieve a therapeutic effect without harmful side effects, as it has been impossible or difficult to administer an accurate dose. Lack of accurate administration has led to varying clinical trial results, and for example FDA being skeptical on approving light therapy devices. Another problem is that little is known about which routes of light treatment are effective. Still another problem is that the knowledge of physiological disorders responsive to light therapy is limited. The present invention provides a solution to overcome or at least alleviate the above problems and drawbacks.

BRIEF DESCRIPTION OF THE INVENTION

The invention provides a new treatment modality for neurological and physiological conditions responsive to bright light. The disclosed treatment modality is a safe, accurately administered, convenient, rapid and effective way of treating these conditions.

The present invention is directed to a method of treating a subject in need of light therapy, said method comprising
 providing a medical device comprising radiation means for directing light via the ear canal of the subject,
 applying the device to the subject, and
 directing non-invasively, intra-cranially via the subject's ear canal bright light having an intensity of 0.7-12 lumens for a treatment time of 1-15 minutes.

The present invention is also directed to a medical device comprising radiation means for directing light via the ear canal of a subject for use in light therapy comprising non-invasive intra-cranial administration of bright light using a light intensity of 0.7-12 lumens for 1-15 minutes.

Specific embodiments of the invention are set forth in the dependent claims. Other objects, details and advantages of the present invention will become apparent from the following drawings, detailed description and examples.

DETAILED DESCRIPTION OF THE INVENTION

The invention primarily provides a dose and secondarily a schedule of intra-cranial administration of bright-light direct-to-brain via the ear canal. The subject to be treated is a mammalian, preferably a human being. The bright light is directed non-invasively at the brain tissue through an external auditory canal of the subject to stimulate the subject's brain tissue. Preferably the light is directed via both ear canals. The ear canal enables accurate administration of bright light to induce the intended therapeutic effect without adverse events as the amount of light exposure is highly controlled.

The bright light treatment is conducted using a medical device comprising radiation means for administering the light non-invasively to the brain tissue via the external auditory canal of the subject to be treated. The medical device may be a portable electronic device, wherein the radiation means comprise an optical radiation source for generating optical radiation, and a light guide for guiding optical radiation from the optical radiation source into the external auditory canal. Optical radiation can be directed by means of a plurality of light units such as leds. The device may further comprise adapter means for arranging the radiation means in the user's external ear to enable ease-of-use and accurate administration of light via the ear canal. According to one embodiment, the radiation means and the adapter means form an ear-piece to be placed on an earlobe. The adapter means are conveniently arranged so that they at least partly penetrate into the external auditory canal. The device may further comprise a controller to adjust bright light administration and optical radiation, for example intensity, time, spectrum and spatial distribution in the brain. One such device is described in WO2008/29001, which is incorporated herein by reference. Other devices may also be used.

The qualities of the light delivered affect the spatial distribution of the light in the brain. According to the invention an intensity of 0.7-12 lumens, typically 1-10 lumens is used. In most cases 3-9 lumens is safe and sufficient for obtaining a clinical effect without adverse effects. In one embodiment an intensity of 4-9, or 6-9 lumens is used. With a light intensity of 1-12 lumens treatment times of 1-15, in most cases 6-12 minutes are suitable and adequate, e.g. 8-12 minutes treatment times are well applicable. The optimal optical radiation dose i.e. the light dose is 3-9 lumens for 6-12 minutes. According to one embodiment the light dose is 6-9 lumens for 8-12 minutes. Naturally a higher light intensity requires a shorter illumination time and vice versa.

Figure 1:
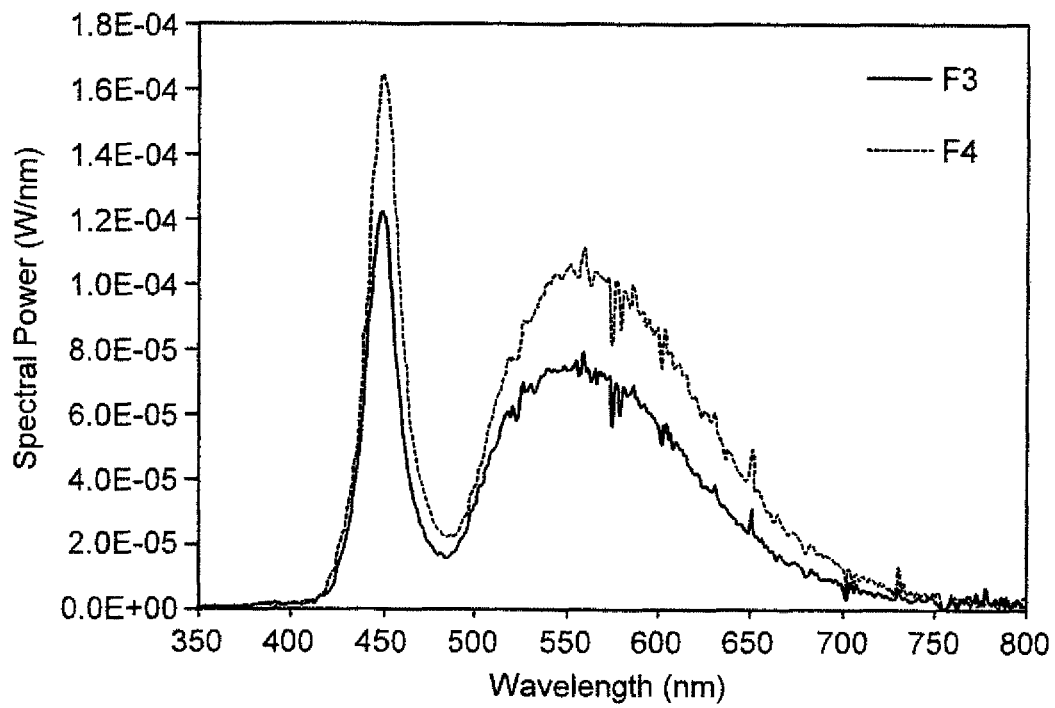
FIG. 1 shows the spectral power distribution of two different fed lights F3 and F4.

The light used in the invention is bright light, which here refers to optical radiation that ranges in the visible spectrum from about 380 nm to about 780 nm, or in adjacent radiation regions of infrared and ultraviolet, which are not visible to the human eye. Typically the light is visible light, and especially light imitating natural sunlight. Illumination via the ear canal with light having a primary light spectrum peak in the blue region i.e. between 450 and 475 nm and a secondary in the green region i.e. between 495 and 570 nm is very effective. One such possible power distribution with a peak at about 465 nm and another at about 550 nm is presented in FIG. 1. The therapeutic effect can be induced by such a spectral power distribution as a whole, or its spectral power peaks, for example the 1.5 E-04 W/nm peak at approximately 465 nm or 1.0 E-04 W/nm peak at approximately 550 nm. The wave length distribution of optical radiation typically changes due to absorption in tissue.

The light therapy is conducted by providing the medical device described, applying the device to a subject in need of such therapy, and directing optical radiation with a light intensity of 0.7-12, typically 3-9 lumens non-invasively to the brain of the subject through an external auditory canal of the subject for 1-15, typically 6-12 minutes to stimulate the brain tissue of the subject.

The above described method of treatment by light therapy may be applied to any disorder or condition that is responsive to such treatment. The present invention especially provides a treatment alternative for a cluster of central nervous system (CNS) conditions, mood disorders, circadian rhythm sleep disorders and inflammatory diseases. CNS conditions as used herein and responsive to light therapy include but are not limited to: seasonal affective disorder (SAD), major depressive disorder (MDD), biopolar affective disorder, obsession compulsive disorder (OCD), migraine, post-traumatic stress, postpartum depression, Alzheimer's disease, Parkinson's disease, and anxiety. Circadian rhythm sleep disorder includes but is not limited to jetlag, shift work sleep disorder, and insomnia. Inflammatory diseases include but are not limited to autoimmune diseases like psoriasis, atopic skin, and skin disorders. Further premenstrual syndrome (PMS), and fertility disorders can be treated with light therapy. The light therapy is believed to optimize or increase dopamine levels in OCD and Parkinson, serotonin levels in e.g. mood disorders, chronic pain and migraine, and noradrenaline/norepinephrine levels in mood and neurological disorders.

Persons suffering from SAD are conveniently treated with the above described light therapy. Typically light having an intensity of 3-9 lumens is administered for 6-12 minutes at least once a day for at least five days a week during the season when SAD is symptomatic. SAD is considered as a sub-type of recurrent MDD, a sub-type of bipolar affective disorder in which depressive episodes regularly begin in one season and remit in another season, or as a sub-type of atypical depression characterized by mood reactivity and being able to experience improved mood in response to positive events. The winter-type of SAD manifests as atypical symptoms of depression that recur in the fall and winter, such as depressed mood, anhedonia, decreased activity, decreased libido, hyperphagia, hypersomnia, carbohydrate carving, fatigue and weight gain. It is believed possible that functional connectivity alterations related to SAD exist in brain regions earlier reported to involve metabolic changes in SAD patients. Epidemiological studies conclude that any population living above 30 degrees northern latitude, or below 30 degrees southern latitude have seasonal symptoms, and that in the US the prevalence correlates to the latitude.

People suffering from migraine constitute another group of patients that are responsive to the light therapy described. The typical migraine headache is unilateral pain (affecting one half of the head) and pulsating in nature, lasting from 4 to 72 hours; symptoms include nausea, vomiting, photophobia (increased sensitivity to light), phonophobia (increased sensitivity to sound), and is aggravated by routine activity. Approximately one-third of people who suffer from migraine headaches perceive an aura-unusual visual, olfactory, or other sensory experiences that are a sign that the migraine will soon occur. It is indeed remarkable that bright light administered intra-cranially via a non-ocular route can prevent migraine attacks or stop an already arousing migraine attack, because generally exposure to bright light via the eyes is considered as a major migraine-triggering factor. Typically light having an intensity of 3-9 lumens is administered for 6-12 minutes once a day to prevent migraine, or 1-6 times daily to relieve a migraine attack.

Usually light therapy treatment, using the light intensity and illumination times disclosed in the present invention, once a day is sufficient to achieve a clinical effect. This once-a-day treatment may be conducted for 1-3 or 1-5 days, or 1-4 or 1-6 weeks, or 1-3 or 1-6 months, or longer, or whenever needed depending on the disorder to be treated. Several daily doses, usually up to three daily doses, may be applied to treating an active migraine attack, fertility disorders, autoimmune diseases, Parkinson's disease, Alzheimer's disease, bipolar affective disease, OCD, or postpartum depression. Low light intensity, starting from 1 lumen may be used in treatments that continue for several weeks and/or for maintenance of a healthy condition.

The effect of the light therapy described may be monitored by analysing resting-state functional connectivity of the human brain. Spatial domain independent component analysis (ICA) may be applied to resting-state functional magnetic resonance imaging (fMRI) data in order to identify changes within the resting state networks (RSNs) that cover the entire cerebral cortex of the test persons. The entire brain cortex may be functionally segmented into a plurality of RSNs. Statistically significant increases in the functional brain connectivity of affected RSNs indicate the response to the light treatment. Changes in magnetic susceptibility correspond with changes in blood-oxygen-level (BOLD) contrasts in the region.

The invention is illustrated by the following non-limiting examples. It should be understood, however, that the embodiments given in the description above and in the examples are for illustrative purposes only, and that various changes and modifications are possible within the scope of the claims.

EXAMPLE 1

Clinical Effect of Light Route and Dose

Different routes of light administration were briefly examined. Brain tissue of 10 subjects with SAD were illuminated via different delivery routes in a dark room and the eyes covered to avoid any ocular stimuli. Illumination was performed with highly targeted leds capable to administer bright light accurately (eye lid, ear, palate, temple) or an array of leds capable to administer bright light more broadly to the illuminated part of the head (palate, temple, back of the head). The response was measured with multiple physiological parameters such as EEG, heart rate, heart rate variation, body temperature and observable physiological changes. Subjects were also asked to evaluate their subjective response to treatment. The results are shown in Table 1.

TABLE 1

| Light administration | |
| --- | --- |
| Route | Result |
| Eye lid | No clinical efficacy comparable to ear route due to eye irritation. For clinical effect, intensity should exceed 3 lumens, which is already riskful for retina (2,7 lumen turned out to be threshold for pain). |
| Palate | No adverse events. Low observed clinical efficacy. Very inconvenient to use, and would cause lowered compliance to treatment. |
| Ear | High clinical efficacy. No adverse events. Easy to use. Auditory canal has the shortest distance to deep brain regions involved in most functions. |
| Below skull edge, at back of the head | No clinical efficacy. |
| Temple | No clear clinical efficacy; treatment focused onto frontal cortex and effects from midbrain, cerebellum, pons etc are not achieved. Non-optimal site to construct a device. |

Light administration via both ear canals using a device as disclosed in WO2008/29001 was chosen for further studies. The dosing study was done with 15 healthy volunteers and 5 SAD sufferers with a device capable of administering different time periods and intensities via the ear canal. Study subjects were lying awake in a silent and dark room with their eyes covered to block any external ocular or audio stimuli. The study was blinded for the subjects: They did not know if they were given bright light and with what parameters. Response to bright light after a daily treatment of maximum one week was assessed with structured interview and real-time monitoring of physiological stimuli such as heart rate, heart rate variation and EEG.

The results obtained with light intensities varying from 1 to 12 lumens, and duration of light exposure varying from 3 to >15 minutes are shown in Tables 2 and 3, respectively. The different light intensities were conducted for 6-12 minutes, and the different duration times were conducted with 3-9 lumens.

TABLE 2

| Light intensity in ear canal | |
| --- | --- |
| Intensity in ear canal | Result |
| 1 lumen | No or not measurable short-term clinical efficacy. |
| 3 lumens | No adverse events. Low observed clinical efficacy. Slight responses would need weeks use. |

TABLE 2-continued

| Light intensity in ear canal | |
| --- | --- |
| Intensity in ear canal | Result |
| 4-6 lumens | High clinical efficacy. Immediate post-treatment subjective observations of psychotropic and cognitive responses. No adverse events. |
| 6-9 lumens | High clinical efficacy. Immediate post-treatment subjective observations of psychotropic and cognitive responses. Some subjects experience headache, dizziness, orthostatic hypotension or similar symptoms. |
| 12 lumens | Most subjects experience symptoms and feeling familiar with sunstroke, headache, dizziness or similar symptoms, orthostatic hypotension and even adverse effect on blood pressure, heat in the ear canal. |

TABLE 3

| Light duration in ear canal | |
| --- | --- |
| Duration | Result |
| 3 min | No clinical efficacy |
| 6 min | No adverse events. First immediate experiences of alertness, "low dose" circadian entrainment and acute anxiolytic effect. Low observed clinical efficacy on severe mood disorders. |
| 8 min | High clinical efficacy. No adverse events. |
| 12 min | High clinical efficacy on severe mood disorders. Some patients experience headache and lightheadness. |
| 12-15 min | Many subjects experience symptoms and feeling familiar with sunstroke, headache, dizziness or similar symptoms, orthostatic hypotension, heat in the ear canal. |
| >15 min | Most subjects experience symptoms and feeling familiar with sunstroke, headache, dizziness or similar symptoms, orthostatic hypotension, heat in the ear canal, nausea and even vomiting. |

The optimal light dose in the above experiments was 3-9 lumens for 6-12 minutes.

Dose response for SAD was further studied in a 3-arm dose response trial, where patients were divided into 0.7 lumen, 4 lumen and 9 lumen light intensity groups. Each group had 30 patients. Each patient was given a respective device to use once a day for 6-12 minutes for 4 weeks at home. The patients were evaluated by a qualified psychiatrist for their level of seasonal depression with Structural Interview Guide for the Hamilton Depression Rating Scale SIGH-SAD at the beginning and at the end of study, and they completed BDI21 self-rating scale weekly at home. The results indicated that up to approximately 80% had symptoms significantly decreasing in each study group. The patients in the 9 lumen and 4 lumen groups remitted significantly faster, typically in 1 to 3 weeks, compared to the 0.7 lumen group who remitted in 4 weeks.

EXAMPLE 2

Clinical Trial with SAD Patients

The optimal dose was later selected into a clinical trial with 13 SAD patients. A pilot prospective study on the putative effect of intra-cranial bright light in the treatment of winter SAD was run.

The light was produced by using phosphor-based white led (465 nm blue light led basis) with a secondary light spectrum peak at 550 nm in a main unit by two 3 W power-LEDs, which is a medical device approved in the European Union, The amount of photic energy was 6.0-8.5 lumens in both ear canals, and the length of treatment was 8 to 12 minutes five times a week during a four-week study period. The patients did not receive any other treatments during the study period.

Subjects were recruited through advertisements in the city of Oulu, Finland (latitude 65°01'N). The final patient series consisted of 13 (aged 37.1±7.2 years) physically healthy indoor workers suffering from major depressive disorder with seasonal pattern according to DSM-IV-TR criteria. Severity of depressive symptoms was assessed using the HAM D-17 and BDI-21. The ethical committee of Oulu University Hospital approved the study protocol.

Figure 2:
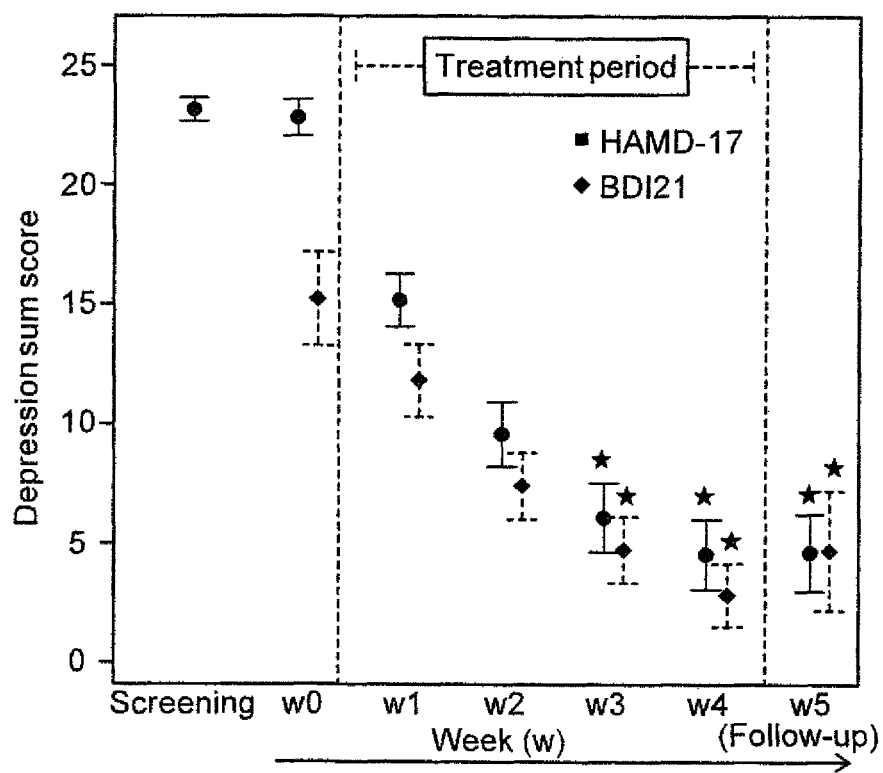
FIG. 2 shows Hamilton Depression Scale (HAMD-17) and Beck Depression Inventory (BDI-21) scores in human subjects treated by intra-cranial brain-targeted bright light via the ear canals. Data is expressed as mean±SEM. Overall treatment effect: HAMD-17, $p<0.001$ and BDI-21, $p<0.001$.

The HAMD-17 mean sum score at screening was 23.1±1.6. Ten out of 13 SAD patients (76.9%) achieved full remission (i.e., HAMD-17 sum score≤7), and 92.3% (12/13) at least 50% reduction in HAMD-17 sum scores at "Week 4". By using a mixed regression model of repeated measures (AR-1) controlling for age, gender, HAMD-17 mean sum score at screening, significant differences were found comparing the HAMD-17 mean sum scores of "Week 0" with the corresponding scores at the "Week 3" (t=−2.05, p=0.045) and "Week 4" visits (t=−2.77, p=0.008) (FIG. 2). Correspondingly, significant differences were found comparing (age and gender controlled) the BDI-21 mean sum scores (15.2±6.7) of "Week 0" with the corresponding scores at the "Week 3" (t=−2.37, p=0.021) and "Week 4" visits (t=−3.65, p<0.001). The results are also shown in FIG. 2.

EXAMPLE 3 fMRI Analysis of the Brain of SAD Patients During Light Therapy fMRI research was conducted to show modulation of the human brain caused by light treatment with the selected, optimal light dose. For provision of reference information applicable in detection of SAD, fMRI was used to collect test data from 45 medication-free subjects with SAD, and 45 age-, gender- (39.78±10.64, 30 ♀, 15 ♂) and ethnicity-matched healthy control subjects (no concomitant medications) from the general population. The test groups were imaged with fMRI using the same test protocol during one winter-period. All subjects with SAD were scanned within one week after they were diagnosed.

During measurements, resting-state BOLD data were collected on a whole body fMRI system with an eight channel receive coil, using a defined sequence (EPI GRE sequence: TR 1800 ms, TE 40 ms, 280 time points, 28 oblique axial slices, slice thickness 4 mm, inter-slice space 0.4, whole brain coverage, FOV 25.6 cm×25.6 cm, with 64×64 matrix, parallel imaging factor 2, flip angle 90°). T1-weighted scans were imaged using 3D FSPGR BRAVO sequence (TR 12.1 ms, TE 5.2 ms, slice thickness 1.0 mm, FOV 24.0 cm, ma-trix 256× 256, and flip angle 20°, and NEX 1) in order to obtain anatomical images for co-registration of the fMRI data to standard space coordinates. For resting state, the subjects were instructed to simply lay still inside the scanner with their eyes closed, think of nothing particular and not to fall asleep. Motion was minimized using soft pads.

ICA was used as a data-driven analysis tool for processing fMRI-generated voxel values. It was shown that by increasing the number of ICA estimated sources, one can probe the entire brain cortex with finely detailed sub-networks. ICA allows differentiating relevant functional brain signals from various sources of noise without a priori knowledge of the signal origin. It also separates noise sources from detected data and then provides spatial maps of functionally independent brain networks.

In the exemplary tests the results revealed that SAD patients compared to age-, gender- and ethnicity-matched healthy control subjects showed statistically significant increases in functional connectivity involving several RSNs. SAD-related increased functional connectivity was shown at two different functional levels while mainly focusing on the detailed RSNs level (70 ICs). Large-scale functional brain networks were localized using low model order ICA of 20 components. Significant increases in functional connectivity were detected in 4 out of 11 identified RSNs in patients with SAD. Segmentation of the brain functionality into detailed sub-networks using a high model order ICA of 70 components yielded 47 RSNs. Significant increases in functional connectivity were detected in 25 RSNs out of the 47 identified networks. Datasets of spatial maps on the detected RNSs and/or of the RNSs of altered functional connectivity are thus applicable as reference information related to a defined physiological disorder, in this example SAD.

EXAMPLE 4

Light Therapy Effect on Migraine

The treatment modality tested was as follows for (a) preventive and (b) attack treatment:

(a) Preventive Treatment
    One daily dose
    6-12 minutes
    3-10 lumens intra-cranial via non-ocular route via each ear canal with a light source in each ear
    Visible light spectrum imitating natural sunlight
    Administered during the day at the time resulting into best patient-evaluated treatment response The most typical feedback was that a daily dose kept the attacks away completely.

Examples of patient feedback for the above mentioned use is given below:

P1 started the light therapy in spring 2010, and almost completely got rid of her migraine attacks. After being without light therapy for a couple of months, the attacks returned. The light treatment functioned as a preventive medicine, but does not cure the attack. Regularly used it prevents the attacks or at least alleviates them.

P2 found that the light treatment kept the migraine attacks away. After no light therapy for five days, the attacks returned.

P3 who was suffering from repeated migraine attacks did not have any attack during the light treatment period.

(b) Migraine Attack in Progress-Treatment
    One to three doses as described in the preventive treatment when the migraine attack is arising or at its full, at intervals depending on individual progression of the migraine attack.

The most typical feedback is that one to three doses when the attack is arousing or in progress aborts the attack or delays it.

Examples of patient feedback for the above mentioned use is given below:

P4 found that he could postpone the migraine attack when he conducted the light therapy in the beginning of the attack.

P5 took medication during a migraine attack, and further conducted light therapy. She found that the light therapy improved the pain-relieving effect during the attack.

P6 found that the light therapy relieved an on-going attack.

EXAMPLE 5

Light Treatment of Jet Lag

In jet lag, the body clock is out of synchronization as it experiences daylight and darkness contrary to the rhythms to which it has grown accustomed to. A number of volunteers tried the light-emitting ear plugs described in WO2008/29001 with a light intensity of 3-9 lumens for 8-12 minutes at about the desired wake-up time at the destination. The feedback has been very positive. Here are two examples:

P7 conducted the light treatment for 8 minutes, 1.5 hours after the desired wake-up time for one week at a destination with 9 hours time difference from the departure. From the very first day onwards she fell no jetlag symptoms, that she usually has, especially the afternoon-dizziness was missing. She continued with the light treatment when back home, and the results were as good. There were no problems this time to get back to the rhythm.

P8 used the same light treatment when travelling from Europe to the American west coast. He did not experience jetlag, and his colleagues were wondering why he was not feeling tired during afternoon meetings.

EXAMPLE 6

Treatment Modalities

The following treatment modalities using intra-cranial administration of bright light via the ear canals with two led lights into two ears with 3-9 lumens (lm) intensity for 6-12 minutes were found effective:

1. once a day for SAD during the season or episode when the disorder is symptomatic;
2. once a day for PMS during the menstrual cycle, or up to five days prior to menstruation, or when individual symptoms start to occur;
3. once a day for migraine as preventive treatment;
4. one to several doses daily when treating migraine seizure/attack;
5. once a day at the desired wake-up time at destination for jet lag or desired alertness time shift work;
6. once a day for post-traumatic stress disorder;
7. once a day for MDD;
8. one to three times a day for OCD;
9. One dose (might be repeated when necessary) for acute treatment in anxiety or anxiety disorder (AD);
10. Once or more times a day to treat acute or chronic inflammation;
11. +1-(−2) h from desired wakeup-time for shift work sleep disorder. If entrainment this way causes too early wakeup, then on the "desired noon". All wavelength with blue spectra and short wavelengths emphasized.

Even lower light intensities may be used for the following indications:

| Indication | Intensity | Timing | Light Properties |
| --- | --- | --- | --- |
| Fertility | 1-9 lm | 1-3 times daily at daytime Light/Dark-ratio enhancement enabled with 2 or more sessions. | All wave-lengths, blue spectra allows smaller intensity in the evening. |
| Autoimmune: psoriasis: atopic skin, skin disorders | 1-9 lm | 1-3 times daily at daytime | All wave-lengths with green spectra emphasized. |
| Alzheimer | 1-9 lm | 1 or more times daily, treatment total energy according to disease severeness. | All wave-lengths with green and infrared emphasized. |
| Bipolar affective disease | 1-9 lm | 1-3 times daily. Morning dose carefully timed according to mood response. | All wave-lengths |
| Postpartum depression | 1-9 lm | 1-3 times daily at daytime | All wave-lengths |
| Anxiety | 1-9 lm | High intensity (4-9 lm) on acute symptoms, lower (1-6 lm) for maintenance. | All wave-lengths |
| Optimizing/increasing dopamine levels in OCD and Parkinson's | 1-12 lm | From 1 (with large intensities) to several (with smaller intensities) times daily. 2 doses (morning + evening) with 3-6 lm threshold to markedly activate substantia nigra and enhance dopamine action in brain. | All wave-lengths |
| Optimizing/increasing 5-HT (serotonin) levels in mood disorders, chronic pain, migraine and other diseases | 1-12 lm | 1-3 times daily. Increased raphe nuclei activity and enhanced monoamine metabolism causing increased 5-HT level also elsewhere in brain, | All wave-lengths |
| Optimizing/increasing noradrenaline/norepinephrine levels in mood and neurological disorders | 1-9 lm | 1-3 times daily. Increased locus caerulus activity. | All wave-lengths |
| Insomnia, difficulty in falling asleep | 1-4 lm or 5-9 lm | Shorter treatment periods with 5-9 lm (1-4 lm/4-12 min, 5-9 lm/1-4 min). 3-0 hrs before bedtime, alternatively morning/daytime use with high doses. | All wave-lengths, blue spectra should be diluted on higher intensities to avoid entrainment if evening dose used. |

The invention claimed is:

1. A medical device for treating a subject for depression, the medical device comprising:

radiation means for directing light directly into an ear canal of the subject suffering from depression, the radiation means including at least one phosphorus-based white light emitting diode ("LED") having a primary peak wavelength in the range of 450-475 nm and a secondary peak wavelength in the range of 495-570 nm;

adapter means for arranging the radiation means in an external ear of the subject to enable administration of light via the ear canal; and a controller unit for adjusting bright light administration and optical radiation provided to the ear canal by the radiation means.

2. The medical device of claim 1, wherein a power intensity in the primary peak wavelength range is substantially 50% higher than a power intensity in the secondary peak wavelength range.

3. The medical device of claim 2, wherein the power intensity in the primary peak wavelength range is about 1.5E-04 W/nm and the power intensity in the secondary peak wavelength range is about 1.0E-04 W/nm.

4. The medical device of claim 1, wherein the radiation means consists of one LED per ear canal of the subject.

5. The medical device of claim 4, wherein each LED is inserted directly into a corresponding ear canal.

6. The medical device of claim 1, wherein the radiation means directs light having an intensity in the range of 3-10 lumens directly into the ear canal of the subject.

7. The medical device of claim 1, wherein the subject is in need of light therapy for prevention of migraine headaches, the light therapy is administered once per day, and wherein the controller unit controls the radiation means to administer a daily light therapy application to the subject directly via the ear canals for a time period in the range of 6-12 minutes, the light having a power intensity in the primary peak wavelength range which is larger than a power intensity in the secondary peak wavelength range.

8. The medical device of claim 6, wherein the daily light therapy application is in the range of 3-10 lumens.

9. The medical device of claim 7, wherein the light of the daily light therapy application has visible light spectrum properties imitating light spectrum properties of natural sunlight.

10. The medical device of claim 7, wherein a power intensity in the primary peak wavelength range is substantially 50% higher than a power intensity in the secondary peak wavelength range.

* * * * *